(12) United States Patent
Basiony

(10) Patent No.: US 10,688,279 B2
(45) Date of Patent: Jun. 23, 2020

(54) SELF-CENTRIC SYMMETRIC CATHETER

(71) Applicant: Mohamed A Basiony, Kenmore, WA (US)

(72) Inventor: Mohamed A Basiony, Kenmore, WA (US)

( * ) Notice: Subject to any disclaimer, the term of this patent is extended or adjusted under 35 U.S.C. 154(b) by 145 days.

(21) Appl. No.: 16/035,216

(22) Filed: Jul. 13, 2018

(65) Prior Publication Data

US 2020/0016367 A1    Jan. 16, 2020

(51) Int. Cl.
*A61M 25/00* (2006.01)

(52) U.S. Cl.
CPC .... *A61M 25/0068* (2013.01); *A61M 25/0026* (2013.01); *A61M 25/0074* (2013.01); *A61M 2025/0034* (2013.01); *A61M 2025/0037* (2013.01)

(58) Field of Classification Search
CPC ............ A61M 25/007; A61M 25/0026; A61M 25/003; A61M 25/0034; A61M 25/0067; A61M 25/0071; A61M 25/0032; A61M 2025/0031
See application file for complete search history.

(56) References Cited

U.S. PATENT DOCUMENTS

| | | | |
|---|---|---|---|
| 7,465,286 B2 * | 12/2008 | Patterson | A61M 25/003 604/43 |
| 8,029,457 B2 * | 10/2011 | Ash | A61M 25/0021 604/43 |
| 8,057,424 B2 * | 11/2011 | Patterson | A61M 25/003 604/43 |
| 8,920,363 B2 * | 12/2014 | Patterson | A61M 25/003 604/43 |
| 8,992,454 B2 * | 3/2015 | Anand | A61M 25/0068 604/5.01 |
| 9,782,535 B2 * | 10/2017 | Anand | A61M 25/0068 |
| 9,849,229 B2 * | 12/2017 | Marsden | A61M 1/3661 |
| 9,861,734 B2 * | 1/2018 | Al Wakeel | A61M 1/285 |
| 10,363,390 B2 * | 7/2019 | Tal | A61M 25/001 |
| 2005/0261663 A1 * | 11/2005 | Patterson | A61M 25/003 604/508 |
| 2013/0324964 A1 * | 12/2013 | Florescu | A61M 25/0032 604/500 |
| 2014/0018772 A1 * | 1/2014 | Ash | A61M 25/0043 604/508 |
| 2015/0306302 A1 * | 10/2015 | Marsden | A61M 1/3661 604/95.04 |
| 2016/0114124 A1 * | 4/2016 | Tal | A61M 25/0029 604/43 |
| 2019/0001099 A1 * | 1/2019 | Smart | A61M 25/0074 |

* cited by examiner

*Primary Examiner* — Matthew F Desanto

(57) ABSTRACT

A hemodialysis self-centric symmetric catheter comprises an elongated portion, a proximal end and a distal end defining a longitudinal axis. Distal end may have two distal segments that may split (separated) from each other with respect to a longitudinal axis at a proximal end of said two distal segments and re-bonded with a distal portion at a distal end of said two distal segments. Each distal segment has a curved portion. Proximal end of said two distal segments may be coupled with a distal end of elongated portion. First distal segment and second distal segment are exactly symmetric (similar) to each other. Each distal segment may have a lumen, a distal tip and a distal angled opening.

7 Claims, 6 Drawing Sheets

SELF-CENTRIC SYMMETRIC CATHETER

BACKGROUND

In hemodialysis application wherein, a blood is withdrawal from a blood vessel for treatment by an artificial kidney device and the treated blood is introduced back into blood vessel.

Various known catheters have been employed to withdrawal a blood from a blood vessel through one lumen of the catheter, then the dialyzed blood is returned to the patient through a second lumen of the catheter.

The most common designs for distal tip of hemodialysis catheters are step-tip, split-tip, symmetric-tip and self-centric curved split-tip. Symmetric-tip catheters have become alternative to conventional step-tip and split-tip catheters for their ability to reverse blood lines during dialysis without an increase in recirculation.

For self-centric curved split-tip catheter, it was designed to automatically center the catheters ports within a blood vessel to reduce fibrin sheath formation, thrombosis and vessel wall occlusions by keeping the tips of the catheter away from the blood vessel wall.

Still there may be drawbacks for above catheters, for example for symmetric-tip catheters, coherent patterns of laminar flow become disrupted by a blood flowing in a direction opposite to a main direction of flow, forming a low-velocity recirculation eddy. The resultant stagnation of a bloodstream can promote thrombus formation and development. Another example of drawback with self-centric curved split-tip catheter is a recirculation in a reverse blood lines configuration which may be more than 20%.

Therefore, it would be desirable to design catheters to may utilize the features of symmetric-tip and self-centric curved split-tip catheters and may reduce the above drawbacks.

SUMMARY

Accordingly, a hemodialysis self-centric symmetric catheter is described to may address the above issues.

The catheter may have a symmetric configuration to utilize the feature of symmetric-tip catheter and may comprise an elongated portion, a proximal end and a distal end defining a longitudinal axis. Distal end may have two distal segments that may splitted (separated) from each other with respect to a longitudinal axis at a proximal end of said two distal segments and re-bonded together with a distal portion at a distal end of said two distal segments. Each distal segment may have a curved portion to utilize the benefits of self-centric curved split-tip catheters. A distal portion may be used to re-bond and fix distal tips of two distal segments again. A proximal end of said two distal segments may be coupled with a distal end of elongated portion.

First distal segment and second distal segment may be symmetric (similar) to each other. Each distal segment may have a lumen, a distal tip and a distal angled opening.

Proximal end of the catheter may attach to a hub with suture wings assembly, which in turn may be connected to extension tubings. Extension tubings may fluidly connect catheter lumens to a blood treatment unit or a dialysis machine.

BRIEF DESCRIPTION OF THE DRAWINGS

The accompanying drawings, which are incorporated in, and constitute a part of the specification, illustrate or exemplify embodiment of the present disclosure and, together with the description, generally explain the principles and features of the present disclosure. The reader should understand that no limitation to the precise arrangement and instrumentalities shown. Modifications, alternation and further application of the principles of the disclosure are also included in the scope of this disclosure. The drawings are briefly described as follows.

DETAILED DESCRIPTION

The following detailed description illustrates the principal of the disclosure by way of example not by way of limitation. While a reference use of the present disclosure describes a self-centric symmetric catheter to be used in hemodialysis, additional non-limiting usage would also include hemofiltration, hemodifiltration, blood adsorption, apheresis, as those of ordinary skill in the art will readily understand.

The hemodialysis self-centric symmetric catheter of present disclosure can be utilized as a short term or long term vascular access for the above treatments and may be made by a biocompatible material like; polyethene, Silicon or any other suitable material. The catheter may also include an anti-microbial coating such as silver, methylene blue and the like. The catheter may be of any suitable size between 6 to 16 French circumferences, or any other suitable size.

The configuration of the catheter may be manipulated to facilitate placement of the catheter into a blood vessel. In one implementation, the catheter may be compressed into a substantially liner profile using a sheath. In an alternative implementation, the catheter may be placed over one or two guidewires with or without stylet/s to facilitate placement of the catheter into a blood vessel.

Figure 1:
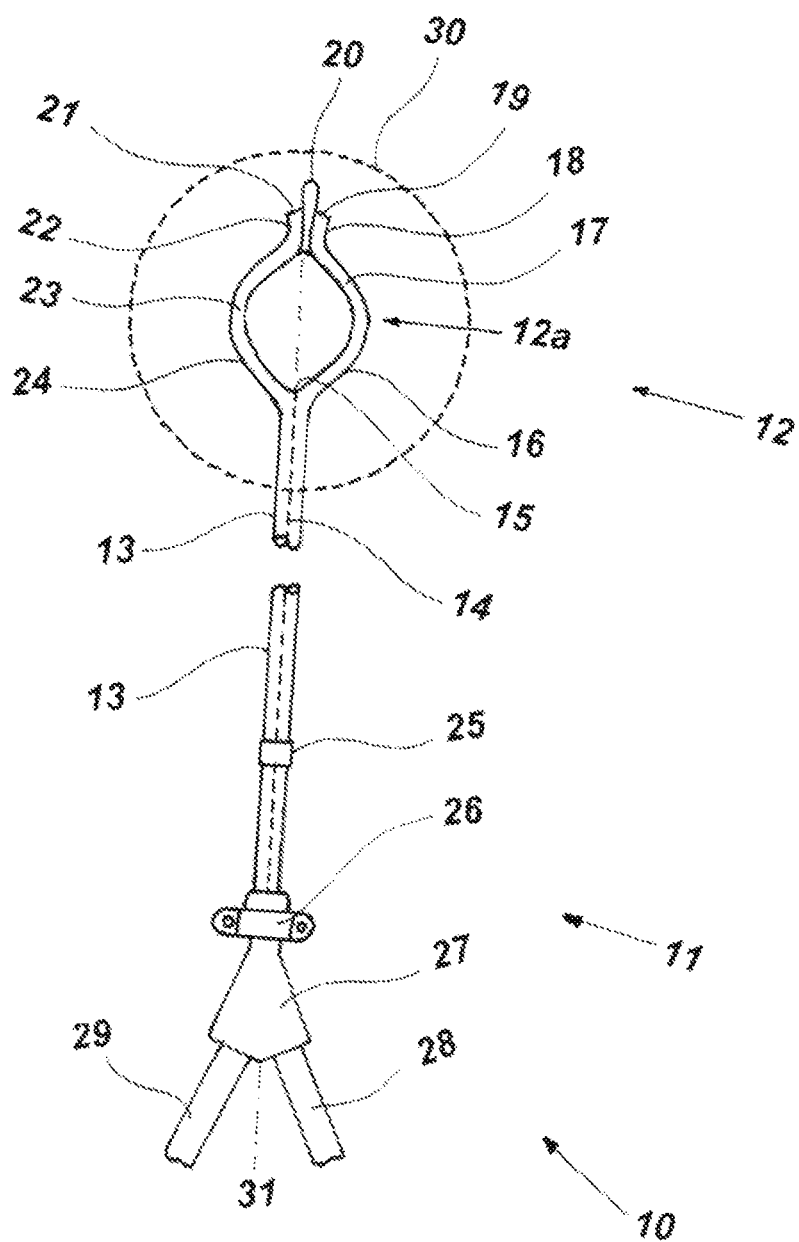
FIG. 1 illustrates a plan view of an exemplary catheter according to the present disclosure.

Now referring to FIG. 1, it illustrates a catheter 10 that may comprise an elongated portion 13, a proximal end 11 and a distal end 12, extended longitudinally to form a longitudinal axis 31. Elongated portion 13 may be a straight or may have a pre-curved configuration and it may extended distally and proximally along a longitudinal axis 31 and may have a bisecting planar septum 14

Proximal end 11 of a catheter 10 may have a cuff 25 (that may be polyester felt or any other material) and a hub 27 with suture wings 26, which in turn may be connected to extensions tubings 28 and 29 as is standard in dialysis catheters. The extension tubes 28 and 29 fluidly connect catheter lumens 17 and 23 to a blood treatment unit or a dialysis machine (not shown for simplicity).

Distal end 12 of a catheter 10 may be splitted (separated) with respect to a longitudinal axis 31 into a first distal segment 16 and a second distal segment 24 at a dividing point 15. First distal segment 16 and second distal segment 24 are exactly symmetric (similar) to each other to utilize the benefit of symmetric-tip catheters for their ability to reverse blood lines during dialysis without an increase in recirculation.

Also, first distal segment 16 and second distal segment 24 may bend (curved) longitudinally outward with respect to a longitudinal axis 31 to form a curved distal configuration 12a to utilize the benefit of self-centric catheters that are automatically center a first distal segment 16 and a second distal segment 24 within a blood vessel to reduce fibrin sheath formation, thrombosis and vessel wall occlusions by keeping a first distal tip 18 with a first distal angled opening 19 and a second distal tip 22 with a second distal angled opening 21 of a catheter 10 away from a blood vessel wall.

A distal portion 20 may re-bond and fix a first distal tip 18 of a first distal segment 16 and second distal tip 22 of a second distal segment 24 together again.

First distal segment 16 may have a first lumen 17, a first distal tip 18 and a first distal angled opening 19. A second distal segment 24 may have a second lumen 23, a second distal tip 22 and a second distal angled opening 21. 30 represents a selectively of a distal end 12. Each distal segment may have a D-shape or circular, or any other shapes in cross section, while elongated portion may have an exterior with generally round, oval, D-shaped or any other shapes in cross section. Also, elongated portion may have an internal longitudinally extending lumen of D-shape, or circular, or any other shapes.

Figure 2:
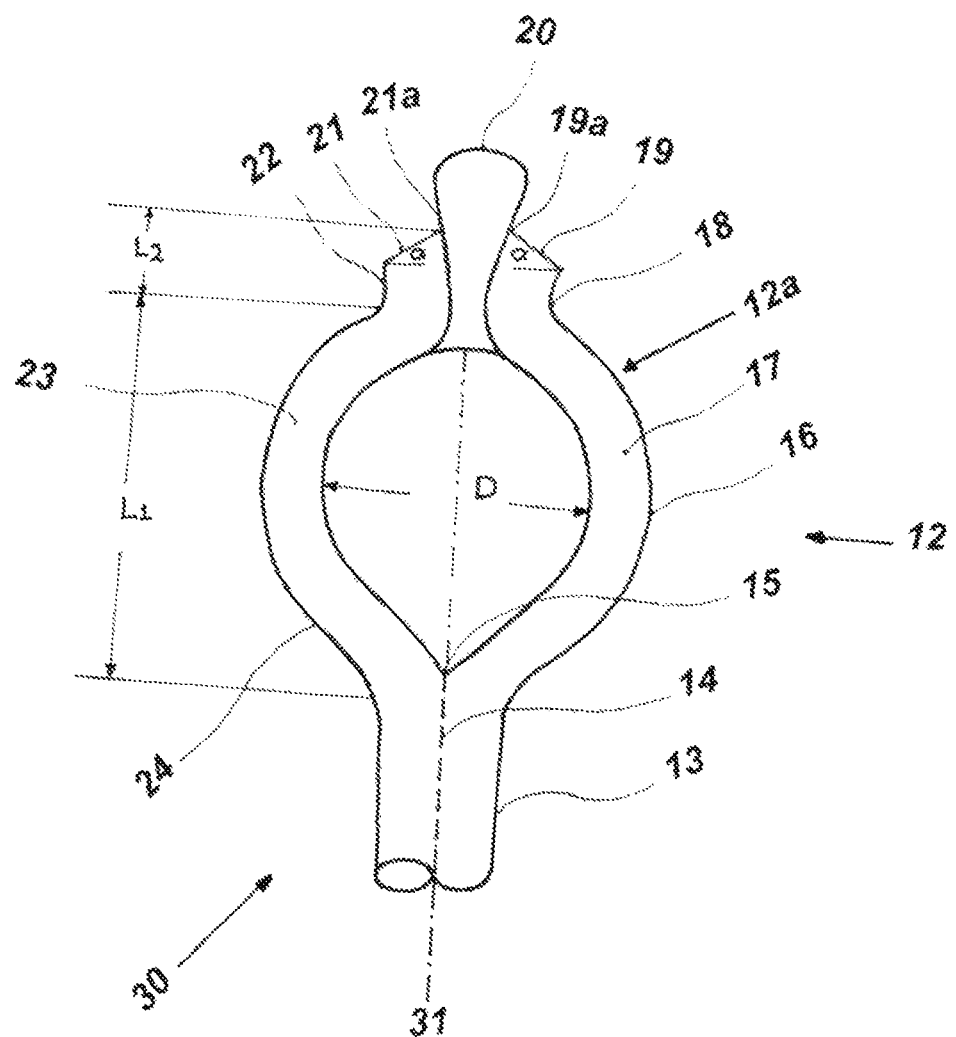
FIG. 2 is a plan view of a distal end of the catheter of FIG. 1 enlarged relative to FIG. 1 according to the present disclosure.

FIG. 2 represents enlarged perspective view 30 of a distal end 12 of a catheter 10 wherein an elongated portion 13 with a bisecting planer septum 14, a first distal segment 16 and a second distal segment 24 that may splitted (separated) with respect to a longitudinal axis 31 at a dividing point 15 and that they may have a curved distal configuration 12a.

First distal segment 16 may have a first lumen 17, a first distal tip 18 and a first distal angled opening 19 with a first angled opening distal end 19a, while a second distal segment 24 may have a second lumen 23, a second distal tip 22 and a second distal angled opening 21 with a second angled opening distal end 21a. First distal angled opening 19 and second distal angled opening 21, each may have an angle "α" with respect to a perpendicular axis to a longitudinal axis 31. Angle "α" may be about 15 degrees to about 65 degrees or any suitable degrees.

"L1" represents a longitudinal length of a curved distal configuration 12a. It may be about 30 mm to about 60 mm or any suitable length. Each distal tip 18 and 22 may have a longitudinal length "L2" which it may be 10 mm or any other suitable length. Diameter "D" of a curved distal configuration 12a may be about 10 mm to about 30 mm or any suitable diameter based on the place of insertion of a catheter 10 if it is in a superior or in an inferior vena cava or in peripheral veins.

Figure 3:
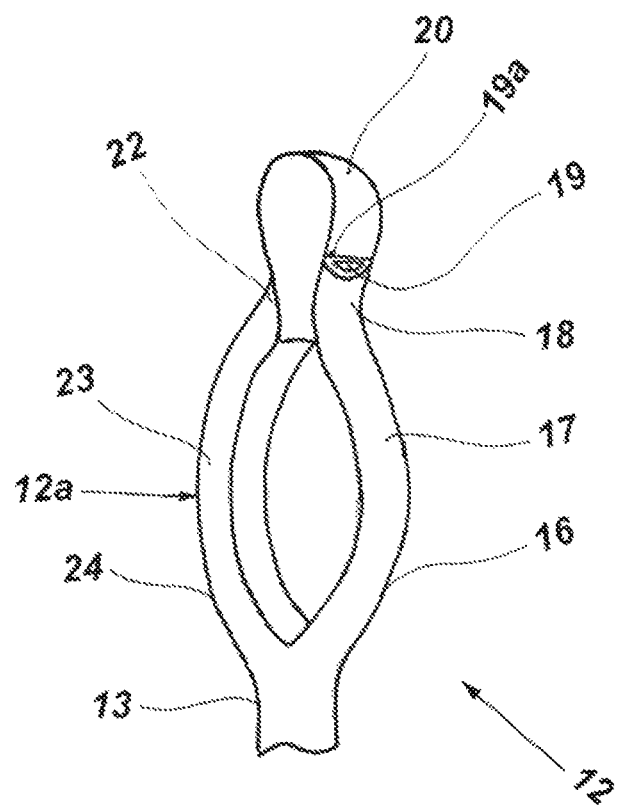
FIG. 3 is a side view of a distal end of the catheter of FIG. 1 enlarged relative to FIG. 1 according to the present disclosure.

FIG. 3 illustrates an enlarged side view of a distal end 12 of a catheter 10 wherein, a first distal segment 16 and a second distal segment 24 that they may have a curved distal configuration 12a. First distal segment 16 may have a first lumen 17, a first distal tip 18 and a first distal angled opening 19 with a first angled opening distal end 19a, while a second distal segment 24 may have a second lumen 23, a second distal tip 22 and a second distal angled opening 21 with a second angled opening distal end 21a (not shown due to a side view)

Figure 4:
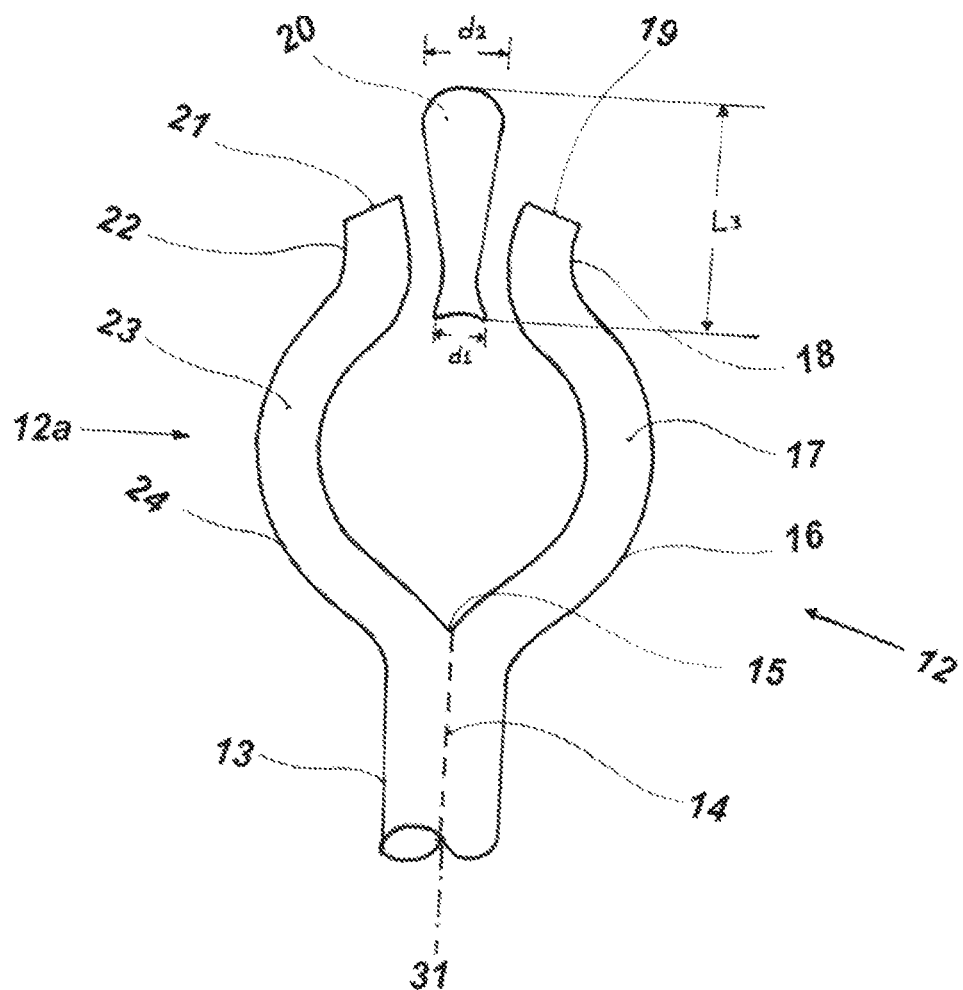
FIG. 4 is an enlarged view of two separated distal segments and a distal portion of the catheter of FIG. 1 according to the present disclosure.

FIG. 4 illustrates an enlarged plan view of a distal end 12 of a catheter 10 with two separated distal segments 16 and 24 before it may re-bonded with a distal portion 20. First distal segment 16 and a second distal segment 24 that may be originally separated at a dividing point 15 to form a curved distal configuration 12a, may re-bond together via a distal portion 20. A distal portion 20 may have a lower distally curved surface with a diameter "d1" and an upper distally curved surface with a diameter "d2". "d1" may be about 1 mm to about 2 mm or any suitable diameter while "d2" may be about 2 mm to about 3 mm or any suitable diameter. In a preferable implementation "d2" may have a larger diameter compare to "d1" and in another implementation they may have the same diameter.

Distal portion 20 may have two side surfaces which may be a slightly curved to fit with a first distal tip 18 and a second distal tip 22 when they may bond together such as by an adhesive or heat sealing or any suitable way. Distal portion may have a length "L3" which it may be about 15 mm to about 20 mm or any other suitable length.

Distal portion 20 may have many features; 1) to bond and fix with two distal tips 18 and 22, 2) to prevent a blood clotting at a second dividing point (not shown for simplicity) which it may formed after re-bond of a first distal segment 16 and a second distal segment 24 directly without a distal portion 20 as with the presence of a distal portion 20, a curve with a diameter "d1" may cover an area formed by a second dividing point to prevent a blood clotting in such a deadly area, 3) to may provide a blood flow separation at a first distal angled opening 19 and a second distal angled opening 21, 4) to may provide less disrupting blood flow in a direction opposite (blood inlet 40) to a main direction of flow (blood outlet 41), and 5) to push main direction of flow (blood outlet 41) away from a blood flow in a direction opposite (blood inlet 40) due to a design configuration of a distal portion 20 wherein a diameter "d1" may be less than a diameter "d2" to bend two distal tips 18 and 22 outwardly with respect to a longitudinal axis 31 to push a blood outlet 41 away from a blood inlet 40.

The rest of components in FIG. 4 are the same as in FIG. 2 and FIG. 3.

Figure 5:
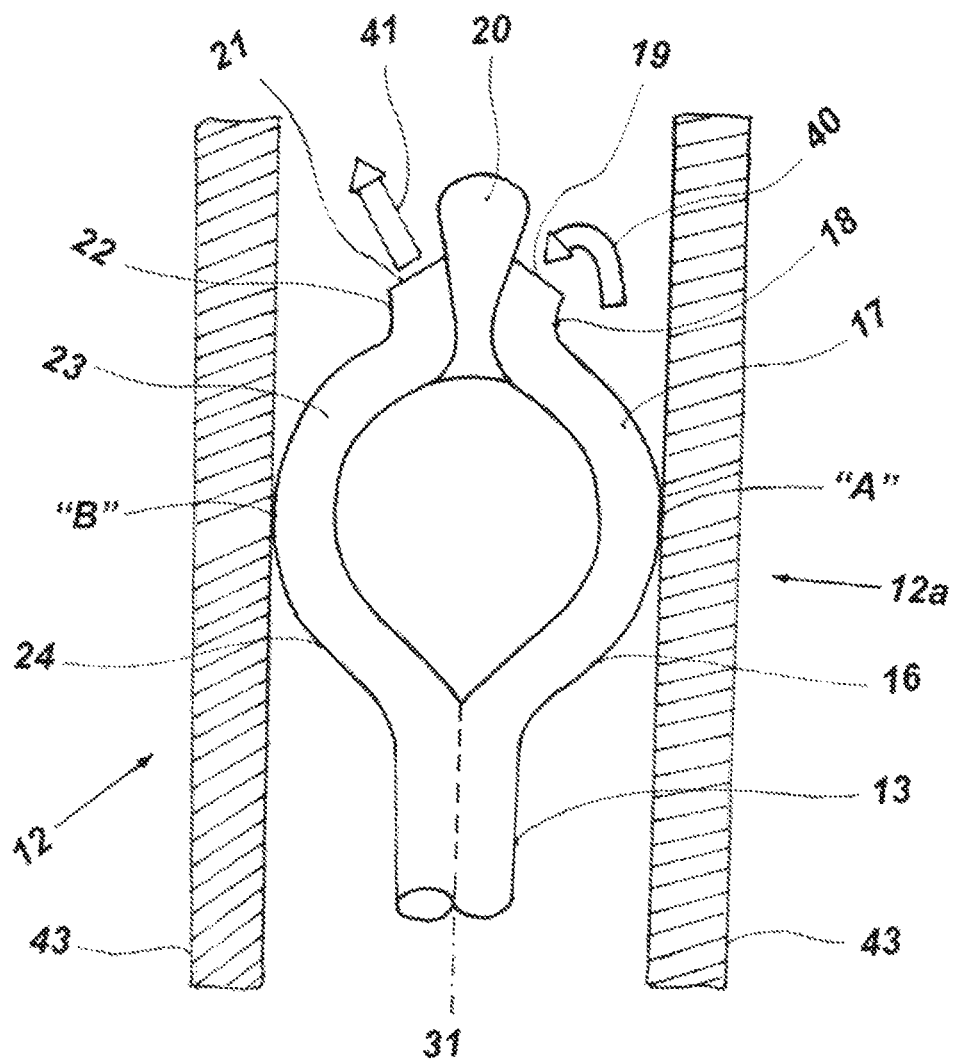
FIG. 5 is an enlarged plan view of a distal end of the catheter of FIG. 1 within a blood vessel wall with a blood inlet and a blood outlet according to the present disclosure.
Figure 6:
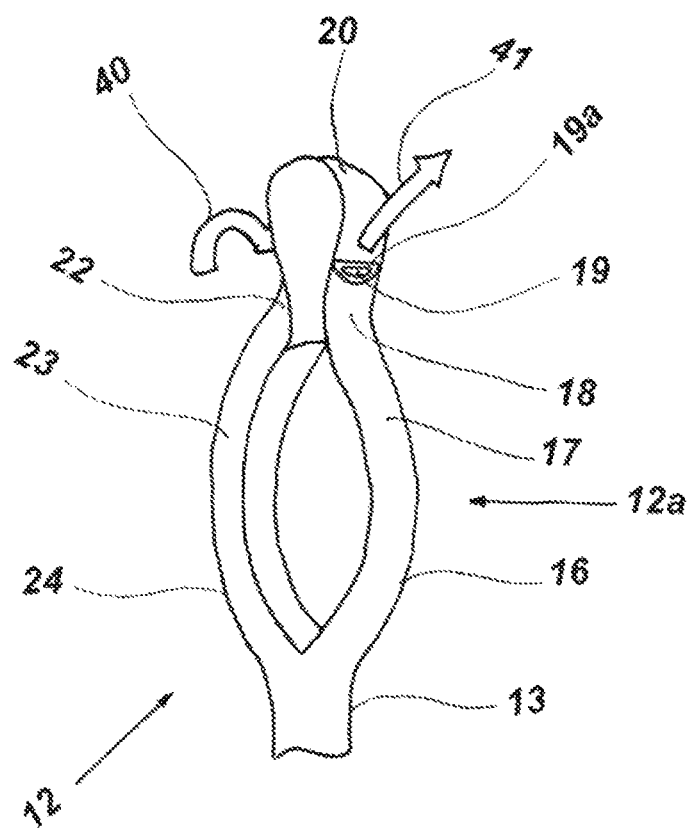
FIG. 6 is an enlarged side view of a distal end of the catheter of FIG. 1 with a blood inlet and a blood outlet according to the present disclosure.

FIG. 5 illustrates an enlarged plan view of a distal end 12 of a catheter 10 with a blood inlet 40 and a blood outlet 41 within a blood vessel wall 43 while FIG. 6 illustrates a side view of a distal end 12 of catheter 10 with a blood inlet 40 and a blood outlet 41. Both FIGS. 5 and 6 illustrate, a first distal segment 16 and a second distal segment 24 that they may have a curved distal configuration 12a with respect to a longitudinal axis 31 (not shown in FIG. 6 for simplicity). First distal segment 16 may have a first lumen 17, a first distal tip 18 and a first distal angled opening 19 with a first angled opening distal end 19a (not shown in FIG. 5 for simplicity), while a second distal segment 24 may have a second lumen 23, a second distal tip 22 and a second distal angled opening 21 with a second angled opening distal end 21a (not shown in FIG. 5 for simplicity and not shown in FIG. 6 as it is a side view). FIG. 5 also illustrates a blood vessel wall 43, a contact point "A" of a first distal segment 16 with a blood vessel wall 43 and a contact point "B" of a second distal segment 24 with a blood vessel wall 43. Those skilled in the art will recognize that contact points "A" and "B" may automatically center first and second distal segments 16 and 24 inside a blood vessel to reduce fibrin sheath formation, thrombosis and vessel wall occlusions by keeping a first distal tip 18 with a first distal angled opening 19 and a second distal tip 22 with a second distal angled opening 21 away from a blood vessel wall 43.

Also, those skilled in the art will recognize that as a diameter "d1" may be less than a diameter of "d2" of a distal portion 20, this may lead to outwardly bend of distal tips 18 and 22 with respect to a longitudinal axis 31. This bend along with the angled configuration of two distal angled openings 19 and 21 and the extension distally of a distal portion 20, those together may provide a separation between a blood inlet 40 and blood outlet 41 and may provide a less disrupting blood flow between a blood inlet 40 and a blood outlet 41, plus the kinetic energy of a blood outlet 41, all together may minimize a blood recirculation generally and also may minimize a low velocity recirculation eddy that may promote thrombus formation and development.

The invention claimed is:

1. A hemodialysis self-centric symmetric catheter comprising:
   an elongated body portion having a longitudinal axis, a proximal end and a distal end;
   the distal end comprising a first splitted curved distal segment having a first lumen, a first distal tip, and a first distal angled opening;
     a second splitted curved distal segment having a second lumen, a second distal tip and a second distal angled opening; and
     a distal portion having a lower proximally curved surface with a first length, an upper distally curved surface with a second length, a first curved side surface bonded to the first distal tip and a second curved side surface bonded to the second distal tip, wherein the first length is less than the second length and the distal portion is configured to bend the first and second distal tips outwardly with respect to the longitudinal axis.

2. The hemodialysis self-centric symmetric catheter of claim 1, wherein the first and second splitted curved distal segments are separated at a proximal dividing point and reconnected via the distal portion at a distal dividing point.

3. The hemodialysis self-centric symmetric catheter of claim 2, wherein each of the first and second splitted curved distal segments have a concave portion with respect to the longitudinal axis in a middle portion that is between the proximal dividing point and the distal dividing point.

4. The hemodialysis self-centric symmetric catheter of claim 2, wherein the lower proximally curved surface of the distal portion and the distal dividing point are configured to prevent blood clotting in an area adjacent the distal portion at the distal dividing point.

5. The hemodialysis self-centric symmetric catheter of claim 1, wherein the catheter has a symmetric configuration with respect to the first and second splitted curved distal segments.

6. The hemodialysis self-centric symmetric catheter of claim 1, wherein the first and second distal angled openings have an angle with respect to a perpendicular axis to the longitudinal axis.

7. The hemodialysis self-centric symmetric catheter of claim 1, wherein the first distal segment and the second distal segment are configured to have a contact point with a blood vessel wall.

\* \* \* \* \*